US008876786B2

(12) United States Patent
Nilsson et al.

(10) Patent No.: US 8,876,786 B2
(45) Date of Patent: Nov. 4, 2014

(54) FLOW CONTROL DEVICE FOR MEDICAL LIQUID

(75) Inventors: Martin P. Nilsson, Hovås (SE); Josef Saltell, Göteborg (SE)

(73) Assignee: Astra Tech AB, Mölndal (SE)

( * ) Notice: Subject to any disclaimer, the term of this patent is extended or adjusted under 35 U.S.C. 154(b) by 271 days.

(21) Appl. No.: 13/094,250

(22) Filed: Apr. 26, 2011

(65) Prior Publication Data
US 2011/0264053 A1    Oct. 27, 2011

Related U.S. Application Data

(60) Provisional application No. 61/328,357, filed on Apr. 27, 2010.

(30) Foreign Application Priority Data

Apr. 27, 2010   (EP) ..................................... 10161164

(51) Int. Cl.
*A61M 5/00*     (2006.01)
*A61M 5/168*    (2006.01)
*A61M 5/14*     (2006.01)
*A61M 39/22*    (2006.01)

(52) U.S. Cl.
CPC ........ *A61M 5/141* (2013.01); *A61M 2005/1405* (2013.01); *A61M 5/168 77* (2013.01); *A61M 2039/229* (2013.01)
USPC ............................................. 604/248; 604/32

(58) Field of Classification Search
USPC ........................... 604/246–256, 30–34, 65–67
See application file for complete search history.

(56) References Cited

U.S. PATENT DOCUMENTS

| 5,906,597 | A | 5/1999 | McPhee |
| 6,270,483 | B1 | 8/2001 | Yamada et al. |
| 6,679,865 | B2 * | 1/2004 | Shekalim ...................... 604/253 |
| 2005/0277883 | A1 | 12/2005 | Kriesel |
| 2006/0195057 | A1 | 8/2006 | Kriesel et al. |

FOREIGN PATENT DOCUMENTS

EP          1 576 976 A2     9/2005

OTHER PUBLICATIONS

European Search Report dated Oct. 25, 2010 Appln. No. EP 10 16 1164.

* cited by examiner

*Primary Examiner* — Kevin C Sirmons
*Assistant Examiner* — Phillip Gray
(74) *Attorney, Agent, or Firm* — Ladas & Parry LLP

(57) ABSTRACT

A flow control device for medical liquid including a housing having an inlet and an outlet, and a channel formed in an inner surface of the housing, the channel extending at least partly in axial direction; a rotatable member rotatable in relation to the housing without being axially displaced, the rotatable member having at least two apertures; and a core member arranged inside the rotatable member, fixedly connected to the rotatable member. A helical flow path is formed between the lateral surface of the core member and the inner surface of the rotatable member, the at least two apertures of the rotatable member being in communication with said helical flow path, and wherein each of the apertures debouches into the channel in at least one rotational position of the rotatable member.

15 Claims, 6 Drawing Sheets

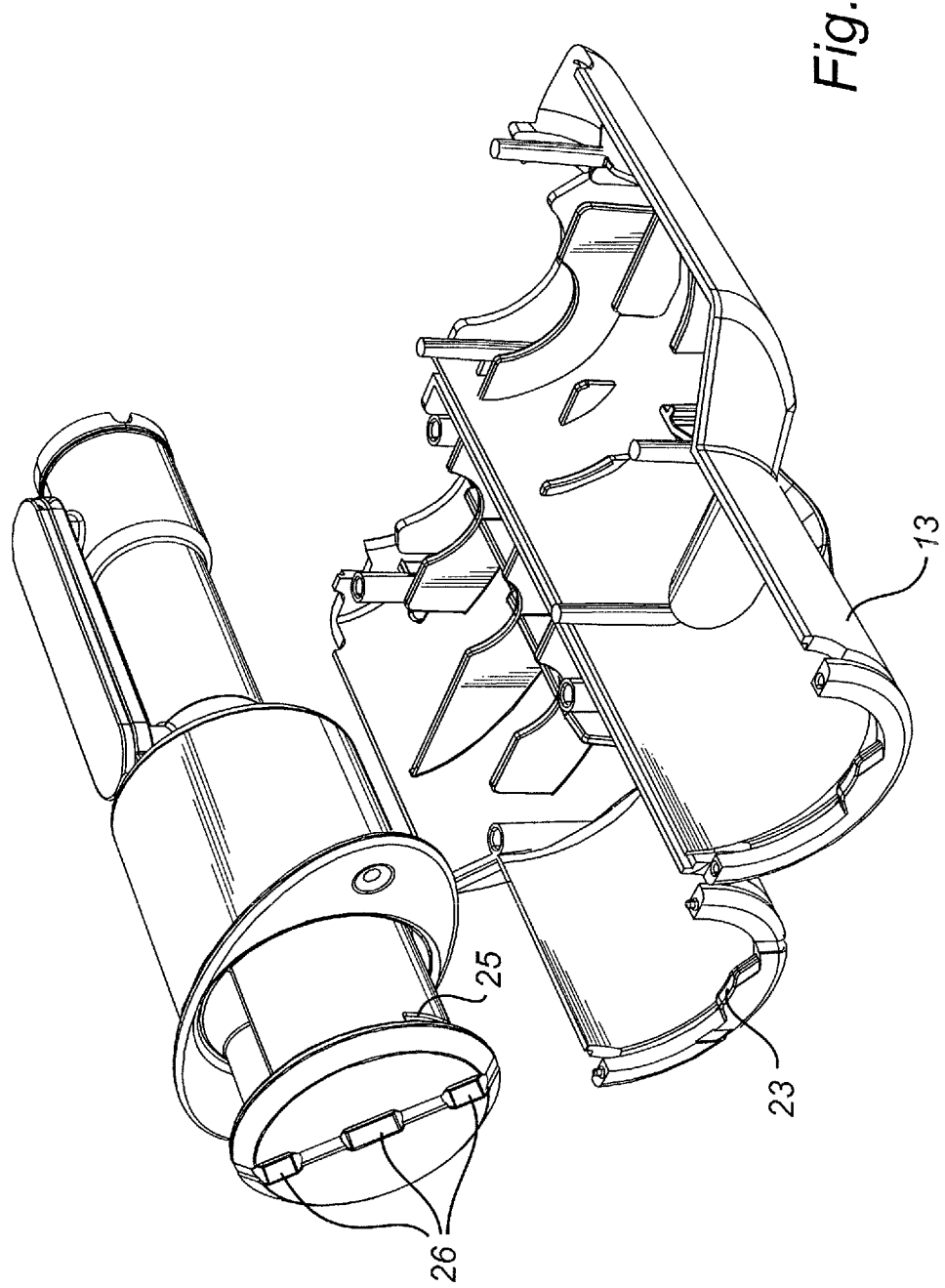

FLOW CONTROL DEVICE FOR MEDICAL LIQUID

TECHNICAL FIELD

The present invention relates to a flow control device for medical liquid.

BACKGROUND OF THE INVENTION

Flow control devices for medical liquid are used for continuously delivering medication, drugs, intravenous solutions and the like to a patient. The flow rate may be adjusted during delivery in order to optimize the flow rate for the current situation, such as a change in a patient's condition.

Conventionally, the flow rate has been adjusted by flow control devices comprising different tubes having different flow restrictions. By selecting through which tube the liquid flows, by means of for example a valve, the flow rate is determined. Or, liquid may flow through several tubes simultaneously for obtaining yet another flow rate to the outlet of the device. Such flow control devices comprise many parts, are relatively big, and are hence complicated and relatively expensive to manufacture. Moreover, these devices conventionally provide only a few flow rates to select from, due to that more available flow rates would require more tubes.

In an attempt to provide a more compact flow control device, the device disclosed in U.S. Pat. No. 6,270,483 comprises a single channel for the liquid flow, which channel can be moved in relation to the inlet part by transferring a rotational movement of a control knob to an axial movement of the channel. The length of the channel from inlet to outlet hence determines the flow rate. Although providing a more compact flow control device than previously known devices, the device is relatively complicated for example requiring a movement conversion mechanism, and it comprises a plurality of parts.

Therefore, there is a need for a flow control device that allows fine regulation of liquid discharge and that is relatively compact and cost-efficient to produce.

SUMMARY OF THE INVENTION

In view of the above mentioned need, a general object of the present invention is to provide an improved compact flow control device. This and other objects are achieved through a flow control device according to the appended claims.

According to the invention, there is provided a flow control device for medical liquid comprising
  a housing having an inlet and an outlet, and a channel formed in an inner surface of the housing, said channel extending at least partly in axial direction;
  a rotatable member rotatable in relation to the housing without being axially displaced, said rotatable member having at least two apertures; and
  a core member arranged inside said rotatable member, fixedly connected to said rotatable member,
  wherein a helical flow path being formed between the lateral surface of the core member and the inner surface of the rotatable member, said at least two apertures of the rotatable member being in communication with said helical flow path, and wherein each of said apertures debouches into the channel in at least one rotational position of the rotatable member, and
  wherein a flow path is formed between the inlet and the outlet of the flow control device, the flow path comprising at least part of the helical flow path and the channel, wherein the flow is controlled by the rotational position of the rotatable member, determining which of said at least two apertures to be in communication with said channel, and thereby determining the length of the helical flow path to be comprised in said flow path between the inlet and the outlet.

The present invention is based on the understanding that the flow rate depends on how long the fluid flow path between the inlet and the outlet is, due to increase in flow restriction with the length of the path. Therefore, the length of the helical flow path to be a part of the total flow path between the inlet and the outlet may be controlled, thereby controlling the flow rate.

By medical liquid should be understood any type of liquid to be introduced through medical tubings, such as catheters, to a patient. This includes various intravenous fluids and solutions for a wide range of medical therapies. In particular, the present invention is suitable for administration of liquid drugs, such as liquid medicaments for pain relief, which are typically administered continuously at very low flow rates during an extended period of time.

A part of the flow path being helix shaped provides for a compact design using space efficiently, such that the helical flow path may be relatively much longer than the length of the core member on which the path is formed. The helix shape also makes it possible to arrange the helical flow path between two parts of the flow control device, for example by molding. The flow control device is rendered even more compact by utilizing one of the parts that forms the helical flow path, i.e. the rotatable member, for determining the length of the helical flow path to be comprised in the flow path.

By means of the present invention, the flow rate becomes easily and precisely controllable. It is also possible to provide various fixed control rates, and thus to adapt the flow control device for various types of use.

Still further, the presently disclosed flow control device is relatively simple and cost-efficient to produce, with relatively few parts. Further, the presently disclosed arrangement is relatively insensitive to tolerances, compared to e.g. conventional capillary flow path arrangements.

The channel preferably extends in an essentially axial direction. However, the channel may also extend also in a circumferential direction, but with at least an axial direction component.

The flow rate may be controlled by changing the position of the at least two apertures of the rotatable member in relation to the channel in the inner surface of the housing, determining the length from the inlet to the outlet of the helical flow path, resulting in a certain flow rate of medical liquid to the patient. An aperture may also be displaced into a position where it is not in communication with the channel so that the aperture does not form an outlet from the helical flow path. Preferably, there are at least three apertures in the rotatable member, each proving an individual flow rate to the patient when being in communication with the channel. Alternatively, two of more apertures may be controlled to be in communication with the channel simultaneously, whereby all liquid medicament that enters the helical path may not be output at the first aperture it meets, so as to allow a part of the liquid medicament to continue to the next aperture forming an inlet to the channel. Alternatively, there may be a plurality of channels that may be in communication with different apertures simultaneously.

Moreover, the core member may be hollow, an inlet through hole to the helical flow path being arranged from the inside of the core member through the wall of the core member into the helical flow path. The inlet through the wall of the core member allows for a smooth flow from the inside of the hollow core member to the flow path on the lateral surface of the core member. The size of the inlet also determines the flow rate of the liquid when it first enters the helical flow path.

Moreover, the apertures may be circumferentially spaced apart and/or axially spaced apart. Each aperture may be positioned to determine the length of the helical flow path to be comprised in the total flow path, and hence the flow rate to the patient. If the apertures are only axially spaced apart and functioning as outlets from the helical flow path one at a time, the channel may be diagonally arranged, although having an axial component.

There are several conditions that require a bolus dose to be administered in regular intervals to the patient, therefore the flow control device may further comprise a bolus container adapted to receive a bolus dose of medical liquid; and a bolus flow path leading to the bolus container branching off from said flow path. Combining a continuous flow to the patient and the possibility to add a bolus is advantageous, since no additional equipment is needed for administration of the bolus dose. Even though a bolus container is added the flow control device may be made compact since the inlet and outlet is combined for both the continuous flow and the bolus dose. The fact that the bolus container fills with a continuous flow provides a controlled bolus dose delivery to the patient in that a bolus dose only can be delivered with a certain interval, corresponding to with which rate the bolus container is filled.

Further, a through hole in the core member and a through hole in the rotatable member may form a bolus inlet to said bolus flow path, whereby liquid medicament may be smoothly introduced into the flow path leading to the bolus container.

Moreover, the bolus flow path may branch off from the flow path before the helical flow path, whereby production of a flow control device with a bolus flow may be simplified, not having to take into account the helical flow path when determining the flow rate toward the bolus container.

Furthermore, a control member may be arranged to empty the bolus container to the outlet providing a controlled delivery to the patient by actuating the control member.

Moreover, the flow control device may further comprise a bolus actuator, and wherein the control member is a one-way valve that opens when subjected to a certain pressure exerted by the bolus actuator, allowing for, by means of for example a plunger, exerting a pressure on the bolus dose toward the valve to open the valve. The bolus actuator may also simplify indication of that the bolus container is filled, by for example protruding to a predetermined level.

Further, the flow control device may comprise a casing adapted to lock the bolus actuator, so as to prevent the bolus container from filling when locked, whereby the bolus container does not fill at all times. This may be desired when treating a patient not requiring regular bolus doses. Moreover, in this way, the bolus dose may not be delivered by accident.

Furthermore, the bolus flow path may extend through a bolus through hole in the rotational member, wherein circular sealings may be arranged between the rotational member and the housing on each side of said bolus through hole, preventing medical liquid to escape from the inlet to the bolus flow path.

The flow control device may further comprise a manipulation key for unlocking or locking said bolus actuator, which may simplify the action of manipulating the bolus actuator.

Moreover, the flow control device may comprise recesses for a manipulation key for rotating said rotatable member, for manual control of the continuous flow rate to the patient. The manipulation key may be removable, to secure that it is not manipulated when a desired flow rate is set, for example by accident.

Further, the rotational member may be hollow and the inlet may be in fluid communication with the inside of the rotational member through a through hole through said rotational member, wherein circular sealings are arranged between the rotational member and the housing on each side of said through hole, to assure that no liquid escapes the desired flow path in connection with the through hole of the rotatable member.

Moreover, a continuous flow rate through the flow control device may be controllable in the range of 0 to 50 ml/h, and preferably in the range of 0 to 20 ml/h. Most preferably, the continuous flow rate is controllable between 2-10, and most preferably 2-5 different predetermined flow rates. For example, the predetermined flow rates may be 0, 5, 7 and 12 ml/h.

BRIEF DESCRIPTION OF THE DRAWINGS

In the following, an embodiment of the present invention will be described in detail, with reference to the accompanying, exemplifying drawings. The same reference numerals are used to denominate similar parts throughout the drawings and the specification.

FIG. 5 is an exploded view of the flow control device and its casing.

DETAILED DESCRIPTION OF PREFERRED EMBODIMENTS

Figure 1:
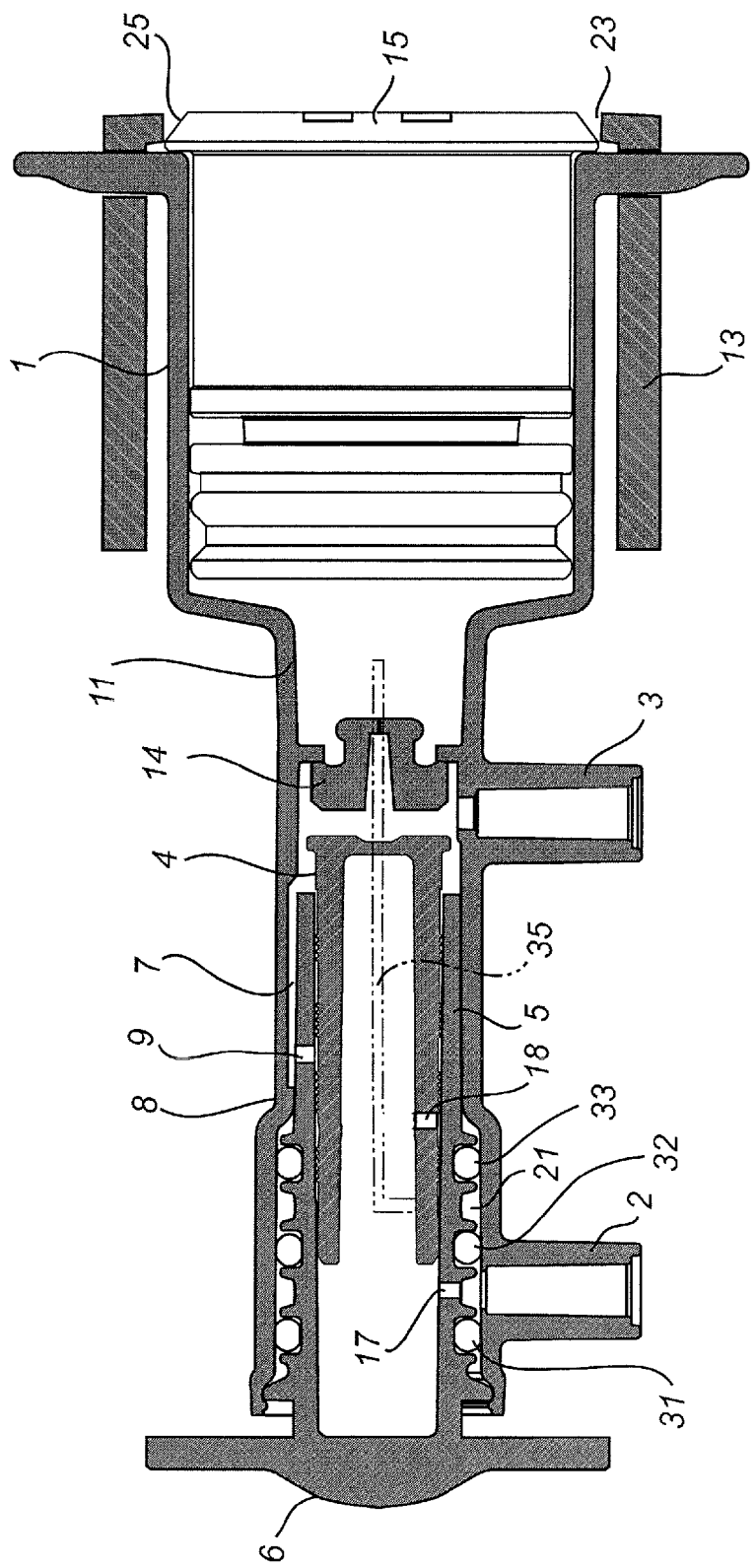
FIG. 1 is a schematic view of the principal construction of a flow control device according to an embodiment of the present invention.

A flow control device 10 for medical liquid, as illustrated in FIG. 1, comprises a housing 1 having an inlet 2, an outlet 3 axially spaced apart from the inlet 2, and a channel 7 formed in the inner surface of the housing 1, connected to the outlet 3. The channel 7 extends essentially axially in the surface. Here, the housing 1 is tubular. There is a hollow core member 4 arranged centrally in the housing 1. The core member 4 is tubular in the illustrated example, and has an open end at the end arranged near the inlet end, which is the end closest to the inlet 2 of the flow control device 10. The open end is adapted to receive liquid, whereas the opposite end of the core member 4 is closed, which end is arranged at the outlet end of the flow control device 10 close to the outlet 3. Here the outlet end is located approximately at the centre (of the axial extension) of the flow control device 10. A rotatable member 5 is arranged between the core member 4 and the housing 1, and is fixedly connected to the core member 4, e.g. integrated with the core member 4. The core member is hence rotatable in accordance with rotation of the rotatable member, but it is not rotatable in relation to the rotatable member, and it cannot be axially displaced. The parts of the flow control device 10 are preferably made of plastic materials. The parts may be injection molded, pressure formed, or the like. More specifically, the housing and the rotatable core member may be formed of polymethacrylate butadiene styrene (such as MMBS). The rotatable member may be formed of polypropylene (PP). It is advantageous to use different materials in the rotatable member and the housing, in order to reduce friction. The sealings may be formed of e.g. EPDM (ethylene propylene diene monomer) rubber. The one-way valve may be formed of e.g. silicone. The inner part of the bolus actuator (see below) may e.g. be made of santoprene TPE grade, and the outer part of the bolus actuator may be formed of polypropene (PP).

A helical flow path 8 is formed between the lateral surface of the rotatable core member 4 and the inner surface of the rotatable member 5. The helical flow path 8 is formed as a helical path along the outer circumference of the core member 4. Here, the circumference of the helical flow path 8 is the same throughout its length. Alternatively the pitch of the helical flow path is increasing or decreasing along the extension of the core member 4, or the width of the helical flow path is increasing or decreasing.

A through hole 17 of the rotatable member 5 leads from the inlet 2 to the core member 4. Two annular sealings 31, 32 are arranged between the rotatable member 5 and the housing 1 on each side of the through hole, to prevent liquid medicament from escaping.

Further, there is an inlet to the helical flow path 8 arranged as a through hole 18 in the wall of the core member 4, leading from the hollow space inside the core member 5 to its surface. There are outlets from the helical flow path 8 arranged as apertures 9 in the wall of the rotatable member 6.

Accordingly, there is a flow path, partly formed by the channel 7 in the inner surface of the housing 1, leading from the inlet 2 at the inlet end of the flow control device 10 to the outlet 3 at the outlet end of the device 10. However, a part of the flow path is the helical flow path 8 formed between the lateral surface of the rotatable core member 4 and the inner surface of the rotatable member 5. The length of the helical flow path 8 to be comprised in the total flow path is determined by which aperture 9 that is currently in communication with the channel 7 of the housing 1, depending on the rotational position of the rotatable member. The length of the total flow path determines the flow rate of the flow control device 10, and is preferably controlled in the range of 0 to 50 ml/h. The flow control is described in more detail in relation to FIG. 2.

Figure 2:
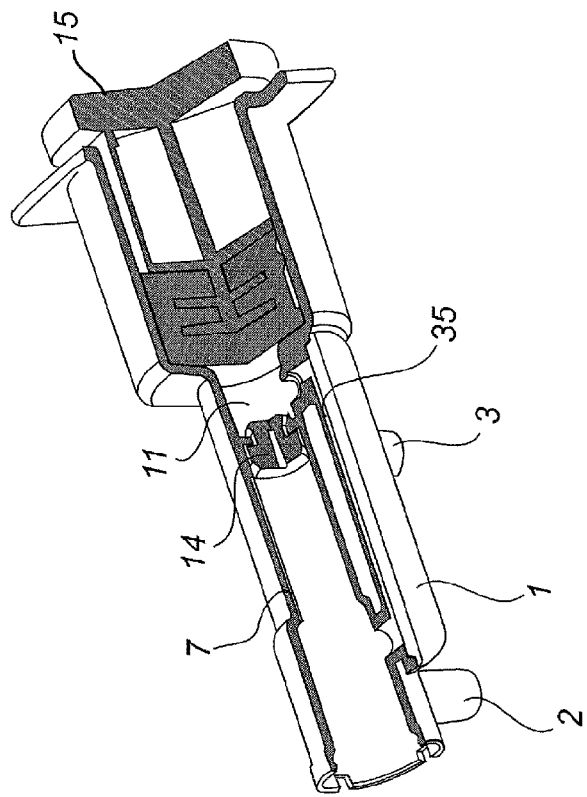
FIG. 2 is an exploded view of the flow control device.
Figure 2:
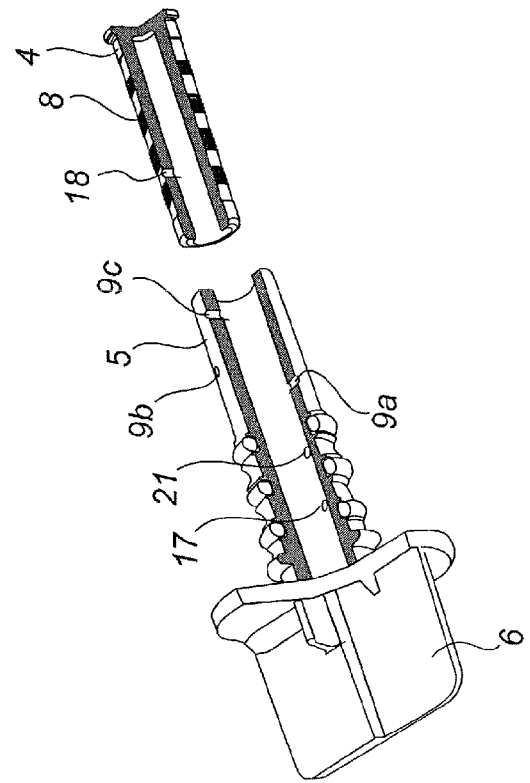

In FIG. 2 the flow control device 10 is illustrated in an exploded view. In the illustrated example, there are three apertures 9*a-c*, axially displaced from each other. Here, in addition to the apertures being axially displaced from each other, they are also circumferentially spaced apart. Alternatively, the apertures are only circumferentially or axially spaced apart.

The apertures 9*a-c* communicate with corresponding positions of the helical flow path 8. In other words, each of the apertures 9*a-c* of the rotatable member 5 may form an outlet from the helical flow path 8, one at a time, when rotated to a position where an aperture is in communication with the channel 7 in the inner surface of the housing 1. The outlet leads via the channel 7 to the flow path toward the outlet 3 of the flow control device 10, and hence to the patient.

In operation, medical liquid, preferably liquid medicament, enters the flow control device 10 through the inlet 2 at the inlet end of the device 10. Thereafter the liquid enters the hollow space inside the core member 4 which fills. The liquid continues through the inlet 18 to the helical flow path 8 and follows the helical path until meeting an outlet from the helical flow path 8, which is formed by the one of the apertures 9*a-c* that is currently in communication with the channel 7. If the aperture 9*c* closest to the outlet end of the core member 4 forms the outlet, the flow rate becomes slower than if another aperture, closer to the inlet end forms the outlet. That is, the longer the liquid travels in the helical flow path 8 the more flow restriction, and accordingly a slower flow rate.

Another flow rate may be selected by rotating the rotatable member 5 and the core member 4, until another aperture comes in communication with the channel 7 to form the outlet. By that means, it is possible to perform fine adjustments of the flow rate. If there are more apertures, even finer adjustments are possible.

Alternatively, all or some of the apertures 9*a-c* may in one or several rotational positions of the rotatable member form an outlet from the helical flow path simultaneously, requiring that the pressure resistance of the first aperture forming an outlet is big enough to allow a portion of the medical liquid to continue toward a second outlet from the helical flow path. However, in this case it may be preferred to provide than one channel in the inner surface of the housing 1, adapted to communicate with the apertures 9*a-c*, and leading toward the outlet 3.

After the liquid has passed through the outlet from the helical flow path 8 it follows the flow path formed by the channel 7 in the inner surface of the housing 1 to the outlet 3 of the flow control device 10. In this way, the liquid may be administered to a patient with a continuous adjustable flow rate.

Figure 3A:
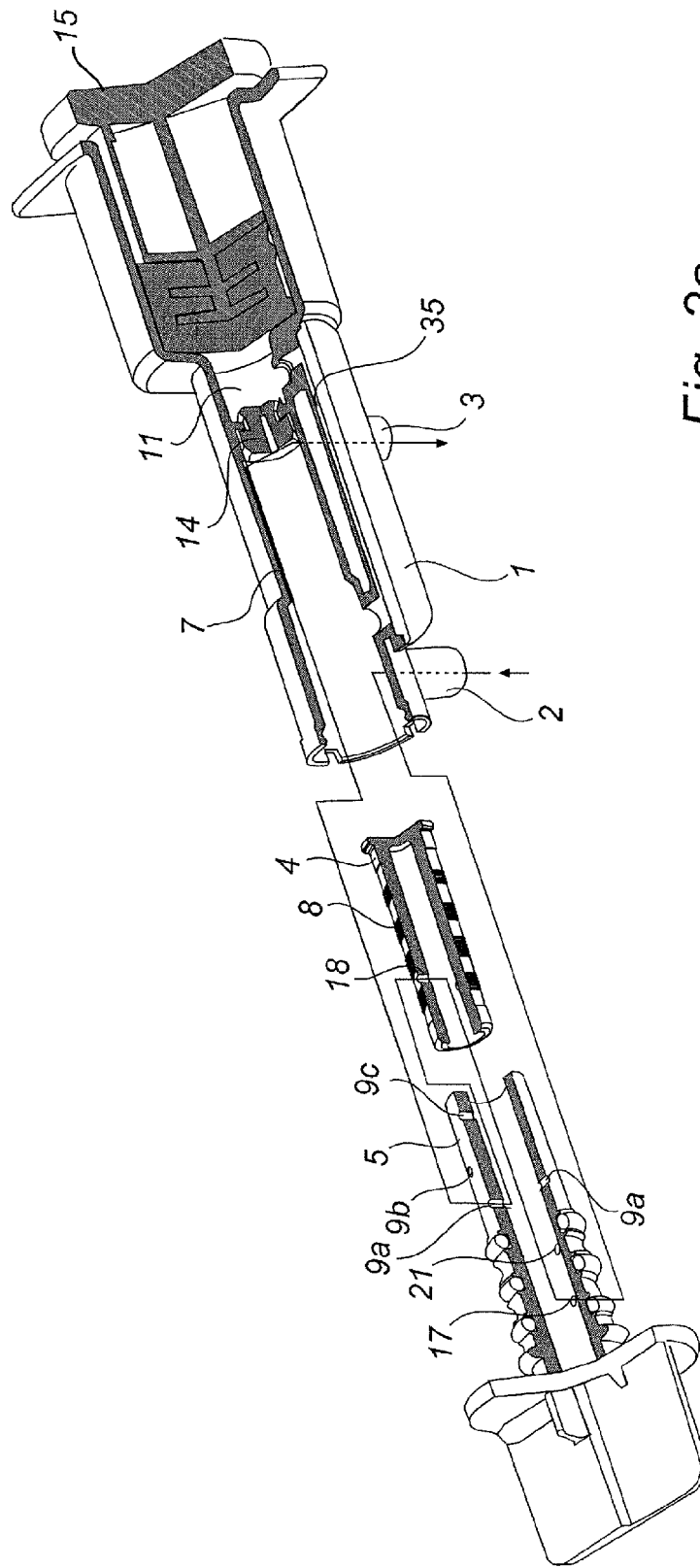
FIG. 3a-b illustrate different flow paths.

Turning to FIG. 3*a* a path for a relatively high flow rate, such as 20 ml/h, is illustrated. The liquid medicament enters at the inlet 2 and enters the hollow core member 4 via the aperture 17 of the core member 4. Thereafter, the liquid flows through the aperture 18 of the core member 4 to the helical flow path 8 which it follows until it after a few turns in the helical flow path 8 meets the aperture 9*a* forming an outlet by communicating with the channel 7 in the inner surface of the housing 1. Thereafter, the liquid continues toward the outlet 3 of the flow control device 10, to the patient.

Figure 3B:
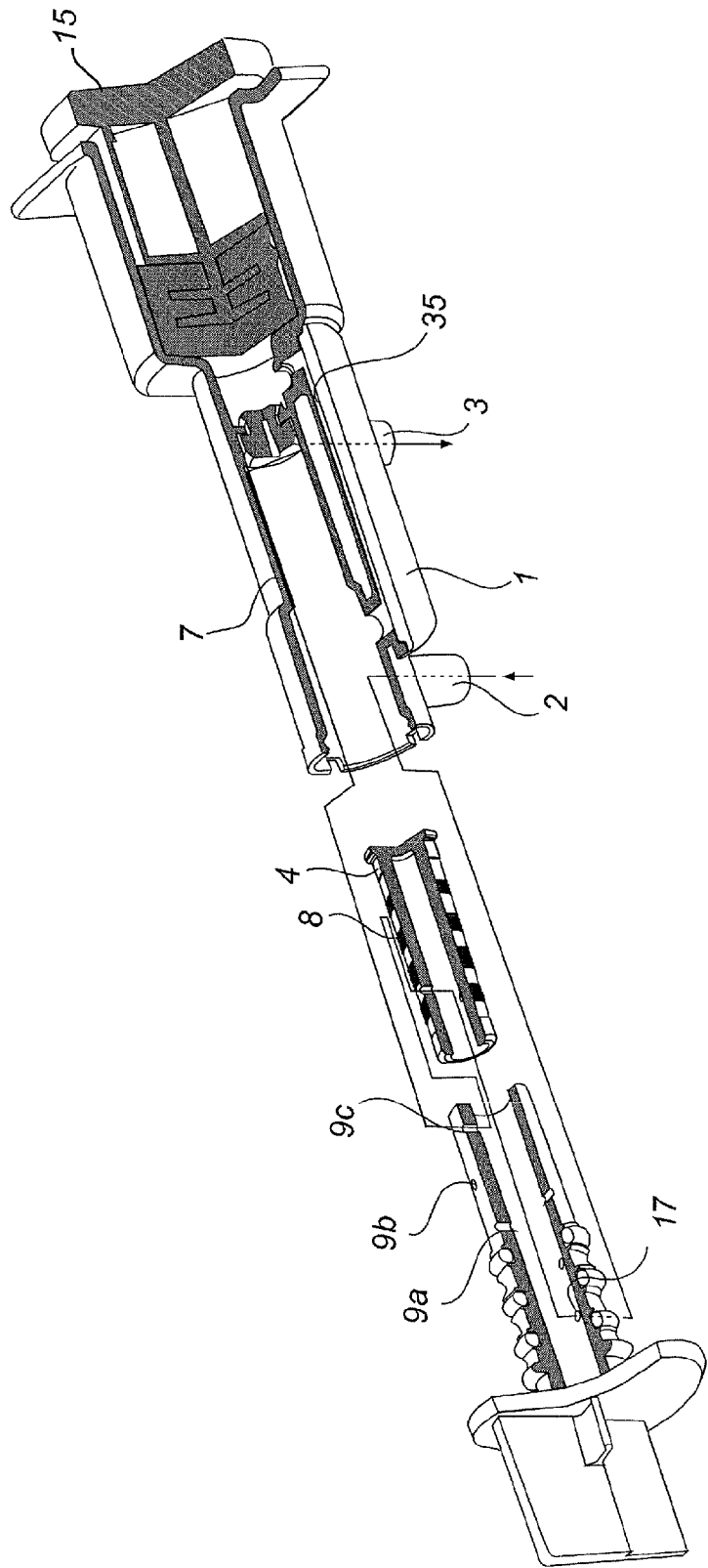

In FIG. 3*b* a path for a relatively low flow rate, such as 5 ml/h, is illustrated. Here, aperture 9*c* is in communication with the channel 7, whereby the liquid medicament follows the helical flow path almost to the end of it. The part of the helical flow path 8 comprised in the total flow path is longer compared to the example illustrated in FIG. 3*a*. The longer flow path the more friction losses, and a lower flow rate is achieved.

Returning to FIG. 1, the flow control device 10 may moreover be adapted to deliver a bolus dose of medical liquid to the patient, typically about 20-50 ml at a time, which is possible with the flow control device 10 illustrated in this example. Accordingly, the flow control device 10 further comprises a bolus container 11 within the housing 1, here, arranged near the outlet 3 at the opposite end of the flow control device 10 from the inlet end. There may be an additional aperture leading from the bore of the core member 4 to the lateral surface of the core member 4, and further through an additional aperture 21 to the bolus path 35. However, preferably, the bolus fluid uses the same aperture 18 as discussed above, and follows a helical path, similar to the discussion above, to the aperture 21. These apertures 18, 21 form an inlet to the bolus flow path 35, ending up at the bolus container 11. The inlet to the bolus flow path 35 is sealed against the housing 1 by means of an annular sealing 33. Here, the bolus flow path 35 is formed by a channel in the inner surface of the housing 1. A one-way valve 14 which is adapted to be opened when subjected to a certain pressure is arranged between the bolus container 11 and the outlet 3. There is a bolus actuator 15, such as an injection plunger for, by actuation such as manual operation, releasing the bolus dose from the container 11. The actuator 15 is arranged at the end of the flow control device 10 on the opposite side of the bolus container 11 relative the outlet end, and protrudes from the device when the bolus container 11 is filled. Moreover, in the illustrated example the casing 13, has two shoulders 23 adapted to engage within corresponding slits 25 formed in the bolus actuator 15, for locking the bolus actuator 15 in position, whereby the bolus container 11 does not fill.

Concerning the bolus dose, in operation, a continuous flow is formed through the bolus apertures 18, 21 in the rotatable core member 4 and the rotatable member 5, respectively, which leads to the bolus container 11 via the bolus flow path 35. The flow rate by which the bolus container 11 is filling is for example defined by the size of these aperture 18, 21, and size and length of the helical path. Typically, it may be desired to administer a bolus dose of liquid medicament to a patient every fifth hour, which requires that the flow rate to the bolus container 11 is sufficient to fill the bolus container within five hours. However, as mentioned, the bolus container 11 may be prevented from filling by locking the bolus actuator 15. When the bolus is to be administered to the patient the bolus actuator 15 is operated so as for the one-way valve 14 to open and add the bolus dose to the continuous flow of medicament toward the outlet 3 of the flow control device 10. The pressure resistance in the inlet to the bolus container 11 from the bolus flow path 35 is bigger than the pressure resistance of the open valve 14.

Figure 4:
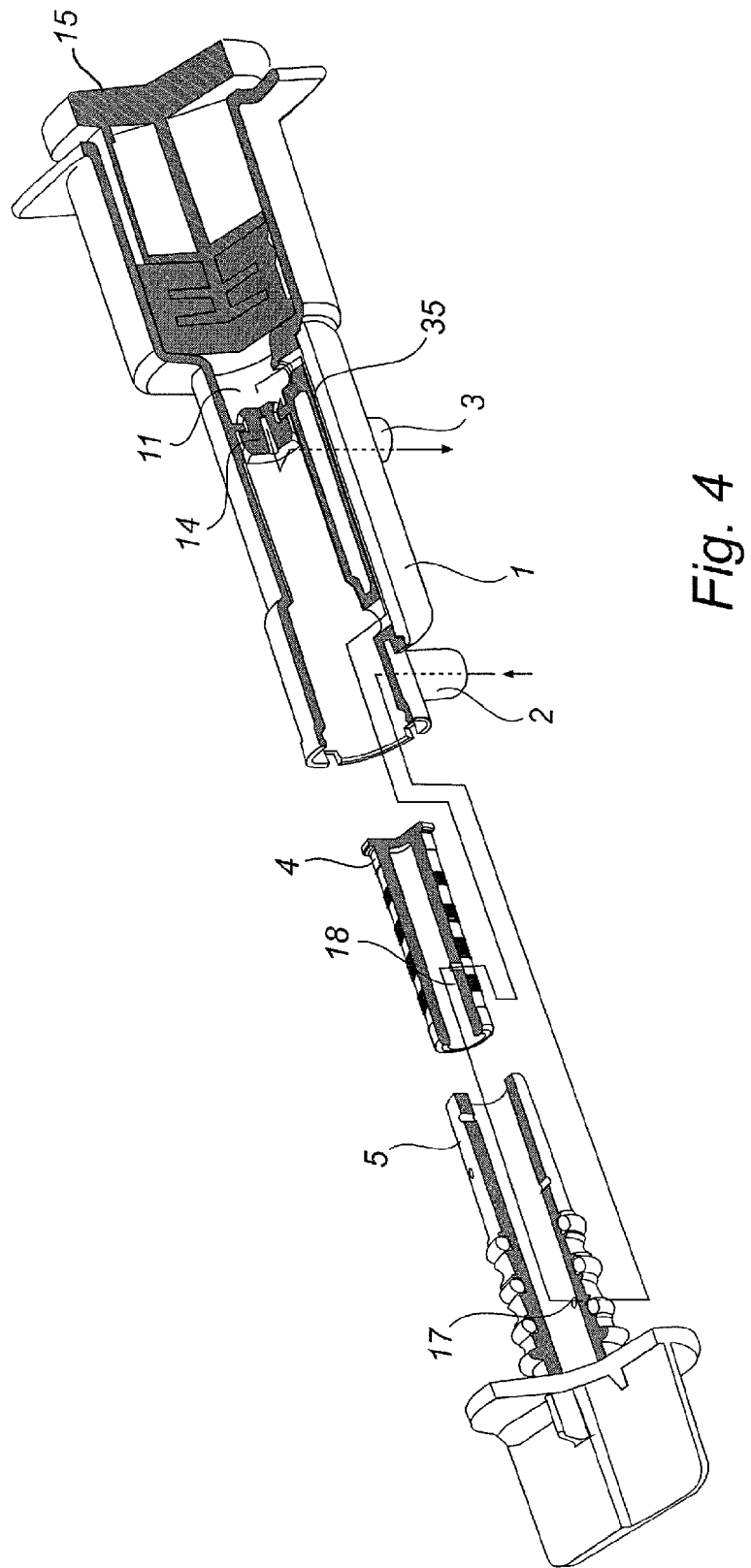
FIG. 4 illustrates the flow path to and from the bolus container.

In FIG. 4 the flow path to and from the bolus container 11 is illustrated. As illustrated in FIG. 3a-b, the medical liquid enters the inlet 2 of the flow control device 10, and enters the hollow core member 4 via the aperture 17 in the rotatable member 5. Thereafter, the medicament for bolus branches off from the flow path, through the aperture 19 of the core member and further through the aperture 21 in the rotatable member, toward the bolus container 11. The medical liquid for bolus collects at the bolus container 11 until the bolus actuator 15 shows, by for example protruding to a maximum level from the flow control device 10, that the bolus container is filled and the bolus dose can be delivered. The bolus container fills slowly, so that a bolus dose can be delivered with relevant intervals, and not too often.

In FIG. 4, the actuator 15 has been operated, by pushing the plunger, toward the one-way valve 14, which has opened due to the exerted pressure. For example, the valve may open when subjected to 0.8 bar compared to an inlet pressure of the flow control device of 0.5 bar. The liquid medicament flows through the valve 14 to the outlet 3 of the flow control device 10.

In each of FIG. 1-4, there is depicted a removable manipulation key 6, here arranged at the end of the flow control device 10, being in engagement with the rotatable member 5. The manipulation key 6 allows manual rotation of the rotatable member 5, and accordingly the integrated core member 4. The key 6 is removable, so that it may be removed and then again returned into engagement with the rotatable member 5, when rotation is required. There may be an indication at the rear end of the rotatable member 5, indicating the current flow rate to the patient, depending on the current rotational position.

In FIG. 5 the casing 13 of the flow control device 10 is illustrated in more detail. The casing 13 has two shoulders 23 adapted to engage within corresponding slits 25 formed in the bolus actuator 15, for locking the bolus actuator 15 in position, whereby the bolus container 11 does not fill. Further, the bolus actuator 15 comprises engagement openings 26 for the removable manipulation key 6 for manually operating the bolus actuator 15 out of, or into, engagement with the casing 13. That is, the manipulation key may be used for controlling the continuous flow rate as well as the filling of a bolus dose.

The person skilled in the art realizes that the present invention is not limited to the preferred embodiment. For example the flow control device may be manufactured without bolus dose possibilities or with a bolus container arranged on the side of the tubular housing. The core member may comprise a plurality of apertures etc.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A flow control device for medical liquid comprising
   a housing having an inlet and an outlet, and a channel formed in an inner surface of the housing, said channel extending at least partly in axial direction;
   a rotatable member rotatable in relation to the housing without being axially displaced, said rotatable member having at least two apertures; and
   a core member arranged inside said rotatable member, fixedly connected to said rotatable member,
   wherein a helical flow path being formed between the lateral surface of the core member and the inner surface of the rotatable member, said at least two apertures of the rotatable member being in communication with said helical flow path, and wherein each of said apertures debouches into the channel in at least one rotational position of the rotatable member,
   wherein a flow path is formed between the inlet and the outlet of the flow control device, the flow path comprising at least part of the helical flow path and the channel, wherein the flow is controlled by the rotational position of the rotatable member, determining which of said at as two apertures to be in communication with said channel, and thereby determining the length of the helical flow path to be comprised in said flow path between the inlet and the outlet, and
   wherein said core member is hollow, an inlet through hole to said helical flow path being arranged from the inside of the core member through the wall of said core member into the helical flow path.

2. The flow control device according to claim 1, wherein the apertures are circumferentially spaced apart.

3. The flow control device according to claim 1, wherein the apertures are axially spaced apart.

4. A flow control device for medical liquid comprising
   a housing having an inlet and an outlet, and a channel formed in an inner surface of the housing, said channel extending at least partly in axial direction;
   a rotatable member rotatable in relation to the housing without being axially displaced, said rotatable member having at least two aperatures;
   a core member arranged inside said rotatable member, fixedly connected to said rotatable member,
   a bolus container adapted to receive a bolus dose of medical liquid; and
   a bolus flow path leading to the bolus container branching off from said flow path;
   wherein a helical flow path being formed between the lateral surface of the core member and the inner surface of the rotatable member, said at least two apertures of the rotatable member being in communication with said helical flow path, and wherein each of said apertures debouches into the channel in at least one rotational position of the rotatable member, and wherein a flow path is formed between the inlet and the outlet of the flow control device, the flow path comprising at least part of the helical flow path and the channel, wherein the flow is controlled by the rotational position of the rotatable member, determining which of said at least two apertures to be in communication with said channel, and thereby determining the length of the helical flow path to be comprised in said flow path between the inlet and the outlet.

5. The flow control device according to claim 4, wherein a through hole in said core member and a though hole in said rotatable member forms a bolus inlet to said bolus flow path.

6. The flow control device according to claim 4, wherein said bolus flow path branches off from said flow path before the helical flow path of the flow path.

7. The flow control device according to claim 4, wherein a control member is arranged to empty said bolus container to the outlet.

8. The flow control device according to claim 7, further comprising a bolus actuator, and wherein the control member is a one-way valve that opens when subjected to a certain pressure exerted by the bolus actuator.

9. The flow control device according to claim 8 further comprising a casing adapted to lock the bolus actuator, so as to prevent said bolus container from filling when locked.

10. The flow control device according to claim 4, wherein the bolus flow path extends through a bolus through hole in said rotational member, wherein circular sealings are arranged between the rotatable member and the housing on each side of said bolus through hole.

11. The flow control device according to any of claim 9 or 10, further comprising a manipulation key for unlocking or locking said bolus actuator.

12. The flow control device according to claim 1 comprising recesses for a manipulation key for rotating said rotatable member.

13. A flow control device for medical liquid comprising
   a housing having an inlet and an outlet, and a channel formed in an inner surface of the housing, said channel extending at least partly in axial direction;
   a rotatable member rotatable in relation to the housing without being axially displaced, said rotatable member having at least two apertures; and
   a core member arranged inside said rotatable member, fixedly connected to said rotatable member,
   wherein a helical flow path being formed between the lateral surface of the core member and the inner surface of the rotatable member, said at least two apertures of the rotatable member being in communication with said helical flow path, and wherein each of said apertures debouches into the channel in at least one rotational position of the rotatable member, wherein a flow path is formed between the inlet and the outlet of the flow control device, the flow path comprising at least part of the helical flow path and the channel, wherein the flow is controlled by the rotational position of the rotatable member, determining which of said at least two apertures to be in communication with said channel, and thereby determining the length of the helical flow path to be comprised in said flow path between the inlet and the outlet, and wherein the rotational member is hollow and the inlet is in fluid communication with the inside of the rotational member through a through hole through said rotational member, wherein circular sealings are arranged between the rotational member and the housing on each side of said through hole.

14. A flow control device for medical liquid comprising
   a housing having an inlet and an outlet, and a channel formed in an inner surface of the housing, said channel extending at least partly in axial direction;
   a rotatable member rotatable in relation to the housing without being axially displaced, said rotatable member having at least two apertures; and
   a core member arranged inside said rotatable member, fixedly connected to said rotatable member,
   wherein a helical flow path being formed between the lateral surface of the core member and the inner surface of the rotatable member, said at least two apertures of the rotatable member being in communication with said helical flow path, and wherein each of said apertures debouches into the channel in at least one rotational position of the rotatable member, wherein a flow path is formed between the inlet and the outlet of the flow control device, the flow path comprising at least part of the helical flow path and the channel, wherein the flow is controlled by the rotational position of the rotatable member, determining which of said at least two apertures to be in communication with said channel, and thereby determining the length of the helical flow path to be comprised in said flow path between the inlet and the outlet, and wherein a continuous flow rate through the flow control device is controllable in the range of 0 to 50 ml/h, and preferably in the range of 0 to 20 ml/h.

15. The flow control device according to claim 14, wherein a continuous flow rate through the flow control device is controllable in the range of 0 to 20 ml/h.

* * * * *